(12) United States Patent
Devassy et al.

(10) Patent No.: US 11,541,374 B2
(45) Date of Patent: Jan. 3, 2023

(54) VANADIUM OXIDE SUPPORTED CATALYST FOR ALKANE DEHYDROGENATION

(71) Applicant: SABIC GLOBAL TECHNOLOGIES B.V., Bergen op Zoom (NL)

(72) Inventors: Biju M. Devassy, Bangalore (IN); Naresh Dhachapally, Bangalore (IN); Nigit J. Meleppuram, Bangalore (IN); Vinod S. Nair, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/273,095

(22) PCT Filed: Sep. 3, 2019

(86) PCT No.: PCT/IB2019/057423
§ 371 (c)(1),
(2) Date: Mar. 3, 2021

(87) PCT Pub. No.: WO2020/049462
PCT Pub. Date: Mar. 12, 2020

(65) Prior Publication Data
US 2021/0339227 A1    Nov. 4, 2021

Related U.S. Application Data

(60) Provisional application No. 62/727,277, filed on Sep. 5, 2018.

(51) Int. Cl.
*B01J 23/22*     (2006.01)
*B01J 21/04*     (2006.01)
(Continued)

(52) U.S. Cl.
CPC ............... *B01J 23/22* (2013.01); *B01J 21/04* (2013.01); *B01J 35/1014* (2013.01);
(Continued)

(58) Field of Classification Search
None
See application file for complete search history.

(56) References Cited

U.S. PATENT DOCUMENTS 3,018,255 A    1/1962  Banks
4,440,631 A *  4/1984  Togari .................... B01J 23/885
                                              502/247
(Continued)

FOREIGN PATENT DOCUMENTS

CN     106582607    4/2017
GB        946583    1/1964

OTHER PUBLICATIONS

Blanco-Bonilla et al., "Vanadium oxides supported on amorphous aluminum phosphate: Structural and chemical characterization and catalytic performance in the 2-propanol reaction" *Journal of Molecular Catalysis A: Chemical* 2016, 416, 105-116.
(Continued)

*Primary Examiner* — Ali Z Fadhel
(74) *Attorney, Agent, or Firm* — Norton Rose Fulbright US LLP

(57) ABSTRACT

A catalyst for non-oxidative dehydrogenation of alkanes and a method for making and using the same is disclosed. The catalyst can include vanadium oxide derived from vanadyl oxalate. More particularly the catalyst is prepared by a method comprising the steps of: (a) contacting a transition alumina support with an aqueous solution comprising a vanadium carboxylate material solubilized therein; (b) heating the contacted alumina support to remove the water and produce a catalyst precursor material in solid form; and (c) heating the solid catalyst precursor material in the presence of an oxidizing source at a temperature of 500 to 800° C. to produce an alumina supported catalytic material comprising vanadium oxide. The catalyst can be further modified with
(Continued)

an alkali metal oxide like potassium oxide, the precursor thereof being introduced with the impregnation solution.

19 Claims, 5 Drawing Sheets

(51) Int. Cl.
*B01J 35/10* (2006.01)
*B01J 37/02* (2006.01)
*B01J 37/08* (2006.01)
*C07C 5/333* (2006.01)

(52) U.S. Cl.
CPC ....... *B01J 35/1019* (2013.01); *B01J 37/0219* (2013.01); *B01J 37/0236* (2013.01); *B01J 37/086* (2013.01); *C07C 5/3332* (2013.01); *C07C 2521/04* (2013.01); *C07C 2523/22* (2013.01)

(56) References Cited

U.S. PATENT DOCUMENTS

| | | | | |
|---|---|---|---|---|
| 5,185,309 | A | * | 2/1993 | Aono ................. B01J 23/22 549/248 |
| 5,220,092 | A | | 6/1993 | Clark et al. |
| 5,510,557 | A | | 4/1996 | Gartside et al. |
| 6,074,984 | A | * | 6/2000 | Demmel ........... B01D 53/8609 502/103 |
| 6,458,970 | B1 | * | 10/2002 | Hefele ................ C07C 51/313 502/209 |
| 8,637,418 | B2 | | 1/2014 | Bruggendick et al. |
| 9,856,200 | B2 | | 1/2018 | Karim et al. |
| 2006/0247446 | A1 | * | 11/2006 | Neto .................... C01G 31/006 549/249 |
| 2007/0213555 | A1 | * | 9/2007 | Neto .................... C07C 51/265 562/888 |
| 2014/0114109 | A1 | * | 4/2014 | Sanchez Valente ..... B01J 37/12 585/658 |
| 2018/0354883 | A1 | * | 12/2018 | Bond ................. B01J 37/0036 |

OTHER PUBLICATIONS

Corma et al., "Preparation of V—Mg—O catalysts: nature of active species precursors" *Applied Catalysis A: General* 1993, 104(2), 161-174.
Del Val et al., "Oxidation of Toluene and o-Xylene on Ti Phosphate-Supported Vanadium Oxide Catalysts" *Journal of Catalysis* 1999, 188(1), 203-214.
Fierro et al., "Structure and activity of silica-supported vanadia catalysts for the oxidation of propylene" *Applied Catalysis* 1983, 6(3), 363-378.
Gorshkova et al., "Physicochemical and catalytic properties of vanadium molybdenum oxide catalyst prepared from vanadyl oxalate" *Kinetika i Kataliz* 1984, 25(1), 201-206 (Abstract provided).
Harlin et al., "Alumina-Supported Vanadium Oxide in the Dehydrogenation of Butanes" *Journal of Catalysis* 2000, 195(1), 67-78.
Hu et al., "Catalytic cracking of n-heptane over HZSM-5 catalysts with the activation of lattice oxygen" *Catalysis Today* 2010, 158(3-4), 504-509.
Hu et al., "Cracking of n-heptane with activation of vanadium oxide based catalyst: effect of support and modification by K or P" *Reaction Kinetics, Mechanisms and Catalysis* 2018, 126(1), 295-306.
International Search Report and Written Opinion issued in Corresponding PCT Application No. PCT/IB2019/057423, dated Nov. 26, 2019.
Lapina et al., "V Solid State NMR Studies of Vanadia Based Catalysts" *Progress in Nuclear Magnetic Resonance Spectroscopy* 1992, 24(6), 457-525.
Matta et al., "Identification of Vanadium Oxide Species and Trapped Single Electrons in Interaction with the $CeVO_4$ Phase in Vanadium-Cerium Oxide Systems. $^{51}$V MAS NMR, EPR, Raman, and Thermal Analysis Studies" *Chem. Mater.* 2002, 14(10), 4118-4125 (Abstract provided).
Qiao et al., "Synthesis of vanadium-based catalysts and their excellent catalytic behaviors on dehydrogenation of $C_4$ hydrocarbons" *Applied Petrochemical Research* 2015, 5, 321-327.
Reddy et al., "Dispersion and 3-picoline ammoxidation investigation of $V_2O_5/\alpha$—$Al_2O_3$ catalysts" *Journal of the Chemical Society, Faraday Transactions* 1991, 87, 1649-1655 (Abstract provided).

* cited by examiner

VANADIUM OXIDE SUPPORTED CATALYST FOR ALKANE DEHYDROGENATION

CROSS REFERENCE TO RELATED APPLICATIONS

This application is a national phase under 35 U.S.C. § 371 of International Application No. PCT/IB2019/057423, filed Sep. 3, 2019, which claims the benefit of priority to U.S. Provisional Patent Application Ser. No. 62/727,277, filed Sep. 5, 2018, the entire contents of each of which are hereby incorporated by reference in their entirety.

BACKGROUND OF THE INVENTION

A. Field of the Invention

The invention generally concerns non-oxidative dehydrogenation of an alkane using a transition alumina supported catalyst that includes vanadium oxide and an optional alkali metal oxide. The catalyst is prepared using a vanadium carboxylate precursor material.

B. Description of Related Art

Alkane dehydrogenation is a recognized process for production of a variety of useful hydrocarbon products, such as isobutylene for conversion to MTBE, isooctane, and alkylates to supplement and enrich gasolines. There are several current catalytic processes useful for catalytic dehydrogenation of light alkanes, including the CATOFIN® process (Houdry, Inc. USA), Oleflex® process (UOP, Inc., USA), and Star Process® (ThyssenKrupp Industrial Solutions AG, Germany). The catalysts that are used in these processes are manufactured from two different groups of materials. The CATOFIN® process utilizes chromia-alumina catalysts. In contrast, the catalysts for the Oleflex® process and Star Process® utilize a supported precious metal. The CATOFIN® process suffers in that the disposal and/or use of a chromium-based catalyst can pose environmental, health, and economic challenges, while the Oeflex and Star processes use expensive metals.

In an effort to overcome these deficiencies, vanadium-based catalysts for alkane dehydrogenation have been developed. By way of example, U.S. Pat. No. 5,220,092 to Clark et al. describes a process for producing alkenes by contacting 3 to 12 wt. % vanadia catalyst supported on a gamma alumina support at temperatures of at least 600° C. for less than 4 seconds. The catalyst was made by impregnating pre-calcined alumina with oxalic acid and ammonium polyvanadate and then calcining at 450° C. to produce an alumina supported divanadium pentoxide.

Volpe et al., (*Journal of the Brazilian Chemical Society*, 2012, Vol. 23, No. 6, 1024-1032) describes the effect of potassium promoters on supported vanadium catalysts. These catalysts were made by soaking alumina with a toluene solution of vanadyl acetylacetonate ($V(AcAc)_3$) dissolved in toluene, removing the support from the toluene, drying the sample and calcining the vanadium soaked alumina support. The calcined catalyst was then soaked with an aqueous solution of potassium nitrate, dried and calcined at about 600° C. to produce a supported potassium vanadium oxide catalyst. The amount of vanadium (V) was 4.8 wt. %. However, these catalysts resulted in less than 20% conversion of n-butane to butene at 823 K (548° C.).

While various supported potassium doped vanadium oxide catalysts are known in the art for the non-oxidative dehydrogenation of alkanes to alkenes, these catalysts suffer from complicated processing steps and/or low catalytic activity or life due to vanadium or potassium aggregates forming during preparation. These aggregates can lead to inactive metal sites on the catalyst surface and/or are prone to deactivate over time due to the formation of coke.

SUMMARY OF THE INVENTION

A discovery has been found that provides a solution to at least some of the problems associated with supported vanadia catalysts with or without an alkali metal dopant. The discovery is premised on preparing the catalyst using vanadium carboxylate, which is soluble in water. Use of a vanadium carboxylate eliminates the use of additional additives and organic solvents. Thus, a more uniform loading of the catalytic metal on the support can be obtained. Furthermore, catalysts with higher surface area can be obtained as compared to catalysts made using organic solvents or ammonium metavanadate.

In one aspect of the invention, methods of making supported non-oxidative alkane dehydrogenation catalysts are described. A method of producing a supported alkali metal/vanadia dehydrogenation catalyst can include (a) contacting a transition alumina support with an aqueous solution that can include water and a vanadium carboxylate material solubilized therein, (b) heating the contacted alumina support to remove the water and produce a catalyst precursor material in solid form, and (c) heating the solid catalyst precursor material in the presence of an oxidizing source at a temperature of 500° C. to 800° C. to produce a catalytic material that includes vanadium oxide. The vanadium carboxylate material can be vanadium monocarboxylate, vanadium dicarboxylate, a vanadium tricarboxylate, or a blend thereof. In a preferred embodiment, the vanadium carboxylate is vanadyl oxalate (e.g., dicarboxylate). Step (b) heating can include heating the contacted alumina support at a temperature of 70° C. to 150° C. Transition alumina can include gamma alumina, chi alumina, kappa alumina, eta alumina, delta alumina, theta alumina, or mixtures thereof. The step (a) solution can include an alkali metal oxide precursor material and the step (c) heating of the contacted alumina can be sufficient to convert the alkali metal oxide precursor to an alkali metal oxide. The catalyst can include 2 to 20 wt. % vanadium oxide, expressed as $V_2O_5$ and based on the total weight of the catalyst. In some instances, the catalyst incudes 0.1 to 2 wt. % of the alkali metal oxide (e.g., potassium oxide) based on the total weight of the catalyst.

In another aspect of the present invention, catalysts for the non-oxidative dehydrogenation of alkanes are described. A catalyst can include vanadium oxide derived from vanadium carboxylate, preferably vanadium oxalate. The catalyst can include an alkali metal dopant, (e.g., potassium, sodium, rubidium, cesium, or alloy, or oxide, or any combination thereof. The catalyst can have surface area of 50 to 160 m²/g. In some embodiments, the catalyst consists of vanadium oxide, potassium oxide, and transition alumina. In a preferred embodiment, the catalyst comprises, consists essentially of, or consists of 2 to 20 wt. % vanadium oxide and 0.1 to 2 wt. % $K_2O$, and 78 to 97.9 wt. % transition alumina.

In yet another aspect of the present invention, processes to dehydrogenate alkanes in a non-oxidative manner are described. A process can include contacting the catalyst of the present invention with a feed source that includes an alkane (e.g., isobutane) at a temperature of 400° C. to 800° C. to produce a product stream that includes an alkene (e.g., isobutene). Contacting can be performed in the absence of oxygen and/or halogenated alkanes. Prior to contacting, the catalyst can be heated to a temperature of 400 to 800° C. in the presence of an oxidizing source. The oxidizing source can be removed, and then the catalyst can be heated to a temperature of 400 to 800° C. in the presence of a reducing source. The feed stream can then be contacted with the hot reduced catalyst to produce the product stream that includes the alkene.

The following includes definitions of various terms and phrases used throughout this specification.

An "alkane" is a linear or branched, substituted or unsubstituted, saturated hydrocarbon. Non-limiting examples of alkane substituents include alkyl, aryl, hydroxyl, alkyloxy, carboxylic acid, ester, amine, amide, nitrile, acyl, thiol, and thioether.

An "aryl" group or an "aromatic" group is a substituted or unsubstituted, mono- or polycyclic hydrocarbon with alternating single and double bonds within each ring structure. Non-limiting examples of aryl group substituents include alkyl, hydroxyl, alkyloxy, carboxylic acid, ester, amine, amide, nitrile, acyl, thiol, and thioether.

An "alkene" is linear or branched, substituted or unsubstituted, unsaturated hydrocarbon. Alkenes include one or more degree of unsaturation. Non-limiting examples of alkene substituents include alkyl, aryl, hydroxyl, alkyloxy, carboxylic acid, ester, amine, amide, nitrile, acyl, thiol, and thioether.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %", "vol. %", or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts and processes of the present invention can "comprise," "consist essentially of," or "consist of" particular ingredients, components, compositions, steps, etc. disclosed throughout the specification. With respect to the transitional phrase "consisting essentially of," in one non-limiting aspect, a basic and novel characteristic of the catalysts of the present invention are their abilities to catalyze non-oxidative dehydrogenation of alkanes.

Other objects, features, and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions of the invention can be used to achieve methods of the invention.

BRIEF DESCRIPTION OF THE DRAWINGS

Advantages of the present invention may become apparent to those skilled in the art with the benefit of the following detailed description and upon reference to the accompanying drawings.

Figure 1:
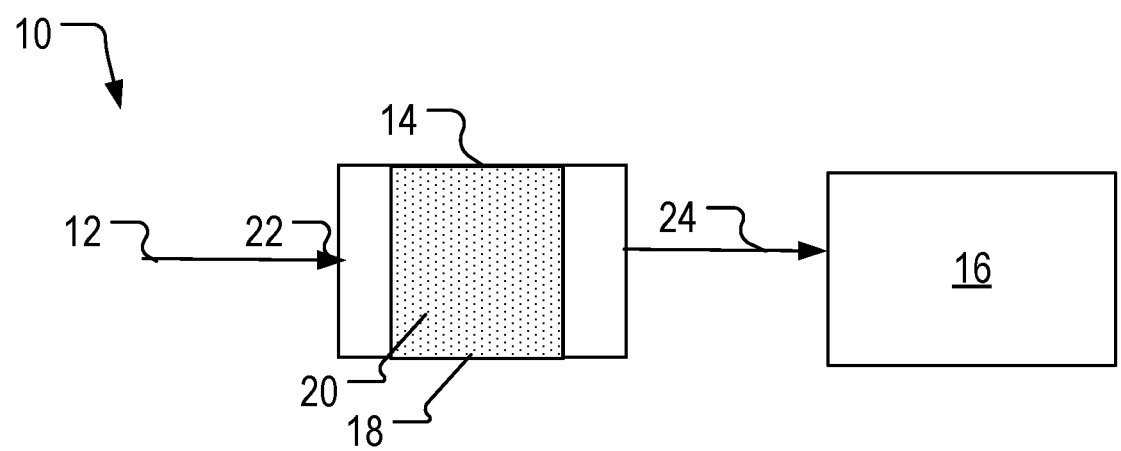
FIG. 1 depicts a system and method of dehydrogenating alkanes to produce alkenes using the catalyst of the present invention.

While the invention is susceptible to various modifications and alternative forms, specific embodiments thereof are shown by way of example in the drawings. The drawings may not be to scale.

DETAILED DESCRIPTION OF THE INVENTION

A discovery has been made that solves at least some of the problems associated with supported vanadia catalysts used in non-oxidative dehydrogenation of alkanes to produce alkenes. The discovery is premised on a more uniform loading of the vanadium precursor on a support material through the use of water soluble vanadium carboxylate materials. This discovery eliminates the use of organic solvents. The produced catalyst has better selectivity than those made using ammonium metavanadate and oxalic acid at the same temperature and pressure.

These and other non-limiting aspects of the present invention are discussed in further detail in the following sections.

A. Method of Producing the Supported Vanadia Catalyst

The supported vanadia alkane dehydrogenation catalyst of the present invention can be made using impregnation techniques. In an impregnation method a certain volume of a metal precursor solution is adsorbed into the pores of the support material. There are two types of impregnation methods that can be used. Wet impregnation includes dipping the support material into an excess amount of metal precursor solution and typically uses an excess of metal precursor solution. Dry or incipient wet impregnation includes contacting a support material with a metal precursor solution of a concentration that corresponds in quantity to the total known pore volume of the support. The contacted material can then be dried and then heated (e.g., calcined) to convert the metal precursor material to a metal oxide and chemically anchor the metal to the support material.

The method of preparing the vanadia catalyst of the present invention can include contacting a transition alumina support with an aqueous solution of vanadium carboxylate material. The transition alumina can include gamma alumina, chi alumina, kappa alumina, eta alumina, delta alumina, theta alumina, or mixtures thereof. The use of transition alumina can facilitate dispersion of the vanadium in the support material. The transition alumina can have surface are of 100 to 250 m$^2$/g, or at least, equal to, or between any two of 100, 105, 110, 115, 120, 125, 130, 135, 140, 145, 150, 155, 160, 165, 170, 175, 180, 185, 190, 195, 200, 210, 220, 230, 240, and 250 m$^2$/g. The alumina can be heat treated in the presence of an oxidizing source (e.g., air, oxygen, or oxygen enriched air) at 70° C. to 150° C., 100° C. to 140° C., 110° C. to 130° C., or 115° C. to 125° C., or any range or value there between or a desired amount of time (e.g., at least 0.5 hours or 1 to 24 hours). The aqueous solution of vanadium carboxylate can be prepared by dissolving a known amount of vanadium carboxylate material in water. Vanadium carboxylate materials include a vanadium (V) oxide complexed with a carboxylate group. Non-limiting examples of carboxylate groups include oxalate $(C_2O_4)^{2-}$, propionate $(CH_3CH_2COO)^-$, malonate $(C_3H_2O_4)^{2-}$, and salicylate $(C_7H_5O_2)^-$, quinaldate $(C_{10}H_6NO_2)^-$, with vanadyl oxalate being preferred. The desired amount of vanadium carboxylate can be added to water at a temperature of 20 to 30° C. until dissolved. The amount of solution is determined based on the pore volume of the catalyst support. In some embodiments, a desired amount of alkali metal precursor solution can be added to the aqueous vanadium carboxylate material. Alkali metal precursor solutions include sodium, potassium, or cesium nitrate, sulfate or halide materials. In a preferred embodiment, potassium nitrate is used. The amount of vanadium precursor and/or alkali metal precursor to be used can be calculated based on the weight percent of vanadium oxide expressed as $V_2O_5$ and alkali metal oxide to be obtained in total weight of final catalyst. In some embodiments, the total amount of metal present in the catalyst can range from 1 to 20 parts by weight of metal per 100 parts by weight of catalyst or from 2 to 12 parts by weight of vanadium oxide per 100 parts by weight of catalyst.

The aqueous vanadium carboxylate solution with or without the alkali metal precursor can be added (contacted) to a known amount of transition alumina support material at 20 to 30° C. (e.g., room temperature). The amount of aqueous solution is determined based on the pore volume of the alumina support. The contacted support material, which includes the vanadium carboxylate precursor material and optional alkali metal precursor material in its pores, can be held at 20 to 30° C. (e.g., room temperature) for a desired amount of time (e.g., 1 to 24 hours, 1 to 20 hours, 1 to 15 hours, preferably 12 hours) and then dried at 70° C. to 150° C., 100° C. to 140° C., 110° C. to 130° C. 110° C. to 130° C., 115° C. to 125° C., or any value or range there between, or about 120° C. until dry (e.g., at least 0.5 hours, 1 to 24 hours, 1 to 20 hours, preferably 16 hours). The dried material can be calcined in the presence of an oxidizing source (e.g., air, oxygen enriched air, or oxygen) at a temperature of 650 to 850° C., 675 to 825° C., 700 to 800° C., 725 to 775° C., or 745 to 755° C. any value or range there between, or about 750° C. to convert the metal precursors (e.g., vanadium carboxylate and optional potassium nitrate) to the corresponding oxides and attach (anchor) the metal to the support material through oxygen metal bonds. The oxidizing source flow rate and temperature ramp can be any value. For example, an air flow rate can be 5 to 10 mLg$^{-1}$ min$^{-1}$ and a temperature ramp rate can be about 1 to 5° C. per minute.

B. Supported Vanadia Catalyst

The catalyst derived from a vanadium carboxylate precursor material and incipient impregnation methodology can include 2 to 20 wt. % of vanadium oxide or at least, equal to, or between any two of 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. % and 20 wt. % of vanadium oxide. In some embodiments, the catalytic material can include one or more vanadium oxides of different valances. In terms of the present disclosure, vanadium oxide can include vanadium (II) oxide (vanadium monoxide, VO), vanadium (III) oxide (vanadium sesquioxide or trioxide, $V_2O_3$), vanadium (IV) oxide (vanadium dioxide, $VO_2$), vanadium (V) oxide (vanadium pentoxide, $V_2O_5$). Vanadium oxide can refer to a vanadate, a compound containing on oxoanion of vanadium generally in its highest oxidation state of +5. The simplest vanadate ion is the tetrahedral orthovanadate $VO_4^{3-}$ anion. Non-limiting examples of vanadate ions include $VO_4^{3-}$, $V_2O_7^{4-}$, $V_3O_9^{3-}$, $V_4O_{12}^{4-}$, $V_5O_{14}^{3-}$, and the like. In addition to these principal oxides of vanadium, various other distinct phases can be present. Phases with the general formula $V_nO_{2n+1}$, wherein n is a whole number greater than zero exist between $V_2O_5$ (vanadium (V) species) and vanadium (IV) species. Examples of these phases include $V_3O_7$, $V_4O_9$ and $V_6O_{13}$. Phases with the general formula $V_nO_{2n-1}$, wherein n is a whole number greater than zero exist between vanadium (IV) species and $V_2O_3$ (vanadium (III) species). Termed Magneli phases, they are examples of crystallographic shear compounds based on rutile structure. Examples of Magneli phases include $V_4O_7$, $V_5O_9$, $V_6O_{11}$, $V_7O_{13}$ and $V_8O_{15}$. Many vanadium oxygen phases are non-stoichiometric. In a preferred embodiment, the vanadium oxide is $V_2O_5$.

Optional amounts of alkali metal oxide can include 0.1 to 0.8 wt. % metal oxide or at least, equal to, or between any two of 0.1 wt. %, 0.2 wt. %, 0.3 wt. %, 0.4 wt. %, 0.5 wt. %, 0.6 wt. %, 0.7 wt. %, and 0.8 wt. % metal oxide. Alkali metals include sodium, potassium rubidium, cesium, or alloys or combinations thereof. In some embodiments, the catalyst can include 2 to 20 wt. % vanadium oxide and 0.1 to 2 wt. % $K_2O$ with the balance being alumina, or 2 to 13 wt. % vanadium oxide and 0.1 to 0.8 wt. % $K_2O$ with the balance being alumina, or 5.5 to 6.5 wt. % vanadium oxide and 0.5 to 0.7 wt. % $K_2O$ with the balance being alumina. In some embodiments, the catalyst only includes 5 to 13 wt. % vanadium oxide, 0.1 to 0.8 wt. % $K_2O$, and 86.2 to 94.9 wt. % transition alumina. The surface area of the catalyst can be at least 50 m$^2$/g or at least, equal to, or between any two of 50, 60, 70, 75, 80, 85, 90, 100, 110, 115, 120, 125, 130, 135, 140, 145, 150, 155, and 160 m$^2$/g.

C. Non-Oxidative Dehydrogenation of Alkanes

The dehydrogenation of alkanes can be carried out by oxidative dehydrogenation or non-oxidative dehydrogenation. Oxidative dehydrogenation can be effected in presence of gas phase oxygen or in the absence of gas phase oxygen using lattice oxygen present in the oxide catalyst. Non-oxidative dehydrogenation is effected both in the absence of gas phase oxygen as well as lattice oxygen. The catalysts of the present invention can be used to in a non-oxidative dehydrogenation of alkane reaction to form an alkene. The alkanes to be dehydrogenated can have the general formula of $C_nH_{2n+2}$ where n is between 2 and 10. The produced alkenes can have a general formula of $C_nH_{2n}$. Non-limiting examples of alkanes include ethane, propane, butane, isobutane, pentane, isopentane, hexane, heptane, octane, nonane, and decane. Alkanes can be obtained from petrochemical processes (e.g., refining operations, chemical reactions, or the like). Non-limiting examples of alkenes include ethene, propene, butene, isobutene, pentene, isopentene, hexene, heptene, octene, nonene, and decene, and all isomers thereof. Non-oxidative dehydrogenation reactions are performed in the absence of oxygen. In some embodiments, the alkane is not halogenated.

Conditions sufficient for alkene production (e.g., isobutylene) include temperature, space velocity, and pressure. The temperature range for alkene production can range from about 400° C. to 800° C., or 550° C. to 700° C., or at least, equal to, or between 400° C., 450° C., 500° C., 550° C., 600° C., 650° C., 700° C., 750° C., and 800° C. A gas hourly space velocity (GHSV) of reactant feed can be higher than 0.1 L $h^{-1}$ $g^{-1}$ or between 0.5 and 10 L $h^{-1}$ $g^{-1}$. The conversion of alkane can be carried out at a pressure of 0.01 MPa to 0.5 MPa, or at least, equal to, or between any two of 0.01 MPa, 0.05 MPa, 0.1 MPa, 0.2 MPa, 0.3 MPa, 0.4 MPa, and 0.5 MPa. The conditions for alkene production may be varied based on the type of the reactor.

The reaction of the methods and system disclosed herein can occur in a fixed bed process or reactor, a circulating catalyst bed process or reactor, or a fluidized bed reactor. The method and system can further include optional collecting or storing the produced alkene (e.g., butylene) product along with using the produced alkene to produce a petrochemical or a polymer.

Referring to FIG. 1, a system 10 is illustrated, which can be used to convert alkanes to alkenes with the vanadium oxide supported catalyst of the present invention. System 10 can include feed source 12 that includes the alkane, reactor 14, and optional collection device 16. The feed source 12 can be in fluid communication with reactor 14 via inlet 22. The alkane feed source can be configured such that it regulates the amount of alkane feed entering reactor 14.

The alkanes (e.g., hydrocarbons having a carbon number of 2 to 10, 3 to 5, or about 4) of the feed stream can be obtained from other process units and/or from commercial sources. The alkane feed stream can include at least 50 vol. %, or 82 vol. % to 95 vol. %, or 88 vol. % to 92 vol. % or 50 vol. %, 51 vol. %, 52 vol. %, 53 vol. %, 54 vol. %, 55 vol. %, 56 vol. %, 57 vol. %, 58 vol. %, 59 vol. %, 60 vol. %, 61 vol. %, 62 vol. %, 63 vol. %, 64 vol. %, 65 vol. %, 66 vol. %, 67 vol. %, 68 vol. %, 69 vol. %, 70 vol. %, 71 vol. %, 72 vol. %, 73 vol. %, 74 vol. %, 75 vol. %, 76 vol. %, 77 vol. %, 78 vol. %, 79 vol. %, 80 vol. %, 81 vol. %, 82 vol. %, 83 vol. %, 84 vol. %, 85 vol. %, 86 vol. %, 87 vol. %, 88 vol. %, 89 vol. %, 90 vol. %, 91 vol. %, 92 vol. %, 93 vol. %, 94 vol. %, 95 vol. %, or any value or range there between of an alkane with the balance being an inert gas. Inert gases include nitrogen, helium, or argon or combinations thereof.

Reactor 14 can include a reaction zone 18 having the supported vanadium catalyst 20 of the present invention. The amounts of alkane in feed source 12, and of catalyst 20 used, can be modified as desired to achieve a given amount of product produced by the system 10. Reactor 14 can be flushed with an inert gas to remove trace amounts of water and/or air. Catalyst 20 can be activated by heating the catalyst at 400 to 800° C. in the presence of an oxidizing source for a desired amount of time (e.g., 0.01 hr to 1 hr). The oxidizing source (e.g., air) can enter reactor 14 through inlet 22 or any other inlet in the reactor. The oxidizing source can be removed by purging reactor 14 with an inert gas. The outlet gas can be monitored to determine the amount of air remaining in the reactor. Once the desired air level is reached, a reducing source (e.g., a gaseous stream containing hydrogen) can be introduced over the catalyst, which can then be heated at 400° C. to 800° C. for a desired amount of time (e.g., 0.01 hr to 1 hr). Feed source 12 can enter reactor 14 and contact heated catalyst 20 to produce product stream 24. Product stream 24 can include an alkene product produced in reaction zone 18. Product stream 24 can exit reactor 14 and enter optional collection device 16 through outlets and inlets (not shown). Optional collection device 16 can be configured to store, further process, or transfer desired reaction products (e.g., alkenes) for other uses. Additionally, any unreacted alkanes can be recycled and included in the reactant feed to further maximize the overall conversion of alkane to alkene (e.g., dehydrogenation). As illustrated in a non-limiting manner in the Examples, the catalyst of the present invention increases the efficiency and commercial value of the alkane conversion process of the present invention as compared to catalysts made with ammonium metavanadate.

Reactor 14 can include one or more heating and/or cooling devices (e.g., insulation, electrical heaters, jacketed heat exchangers in the wall) or controllers (e.g., computers, flow valves, automated values, etc.) that are used to control the reactant flow, reaction temperature, and/or pressure of the reaction mixture. While only one reactor is shown, it should be understood that multiple reactors can be housed in one unit or a plurality of reactors housed in one heat transfer unit.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Comparative Example 1

Synthesis of Comparative Vanadium Oxide/$K_2O$ Supported Catalyst

Transition alumina support in the form of spheres (~2.5 mm diameter) procured from Sasol Ltd. (South Africa) with surface area of 137 $m^2/g$ was used for catalyst preparation. The alumina support (about 100 g) was dried an oven at 120° C. for 16 hours in the presence of air to remove moisture. The dried alumina support, after cooling to room temperature, was used for catalyst preparation by incipient wetness impregnation method. The catalyst was prepared by incipient wetness impregnation of the support with an aqueous solution of ammonium metavanadate dissolved in oxalic acid. The required quantity of ammonium metavanadate (AMV, 4.06 g) was added to DM water (based on pore volume of 0.45 mL/g) and the solution was heated at 40° C. After that, a calculated amount of oxalic acid dihydrate (OA, 4.69 g) was added to the AMV solution under stirring (OA/AMV=1.5). After addition of the OA, the AMV solid started to dissolve and the mass color had changed from yellow to green and finally to blue color. Finally, the obtained clear solution was ammonium vanadyl oxalate having a blue color. The required quantity of potassium nitrate (0.64 g) was dissolved in ammonium vanadyl oxalate solution. The impregnation was carried out by contacting the impregnation solution with the alumina (46.16 g) support at room temperature. The impregnated alumina support was then kept at room temperature for 12 hours and then dried at 120° C. for 16 hours. The dried sample was then calcined at 750° C. for 4 hours in air (flow rate, 8 ml g$^{-1}$ min$^{-1}$). After calcination, the catalyst was cooled in presence of air and the catalyst was stored in an airtight container. The final calculated composition of the catalyst corresponds to vanadium oxide—6.3 wt. %, K$_2$O—0.6 wt. % with remaining part comprising transition alumina.

Comparative Example 2

Synthesis of Comparative Vanadium Oxide/K$_2$O Supported Catalyst

Transition alumina in the form of spheres (~1.8 mm diameter) procured from Sasol with surface area of 207 m$^2$/g was used for catalyst preparation. The alumina support (about 100 g) was heat treated in an oven at 120° C. for 16 hours in the presence of air. The dried alumina support, after cooling to room temperature, was used for catalyst preparation by incipient wetness impregnation method. The catalyst was prepared by incipient wetness impregnation of the support with an aqueous solution of ammonium metavanadate dissolved in oxalic acid. The required quantity of ammonium metavanadate (AMV, 7.72 g) was added to DM water (based on pore volume of 0.85 mL/g) and the solution was heated at 40° C. After that, a calculated amount of oxalic acid dihydrate (OA, 8.92 g) was added to the AMV solution under stirring (OA/AMV=1.5). After addition of the OA, the AMV solid started to dissolve and the mass color had changed from yellow to green and finally to blue color. Finally, the obtained clear solution was ammonium vanadyl oxalate having a blue color. The required quantity of potassium nitrate (0.64 g) was dissolved in ammonium vanadyl oxalate solution. The impregnation was carried out by contacting the impregnation solution (39.3 mL) with the alumina (50 g) support at room temperature. The impregnated alumina support was then kept at room temperature for 12 hours and then dried at 120° C. for 16 hours. The dried sample was then calcined at 750° C. for 4 hours in air (flow rate, 8 ml g$^{-1}$ min$^{-1}$). After calcination, the catalyst was cooled in presence of air and the catalyst was stored in an airtight container. The calculated composition of the catalyst corresponds to vanadium oxide—12 wt. %, K$_2$O—0.6 wt. % with remaining part comprising transition alumina.

Example 3

Synthesis of Vanadium Oxide/K$_2$O Supported Catalyst of the Present Invention

Transition alumina support in the form of spheres (~2.5 mm diameter) procured from Sasol with surface area of 137 m$^2$/g was used for catalyst preparation. The alumina support (about 100 g) was heat treated in an oven at 120° C. for 16 hours in the presence of air. The dried alumina support, after cooling to room temperature, was used for catalyst preparation by incipient wetness impregnation method. The catalyst was prepared by incipient wetness impregnation of the support with an aqueous solution of vanadyl oxalate. The required quantity of vanadyl oxalate (3.97 g) and potassium nitrate (0.39 g) was dissolved in water and used for incipient wetness impregnation. The impregnation was carried out by contacting the impregnation solution (12.6 mL) with alumina support (27.93 g) at room temperature. The impregnated alumina support was then kept at room temperature for 12 hours and then dried at 120° C. for 16 hours. The dried sample was then calcined at 750° C. for 4 hours in air (flow rate, 8 ml g$^{-1}$ min$^{-1}$). After calcination the catalyst was cooled in presence of air and the catalyst was stored in an air tight container. The calculated composition of the catalyst corresponds to vanadium oxide—6.3 wt. %, K$_2$O—0.6 wt. % with remaining part comprising transition alumina.

Example 4

Synthesis of Vanadium Oxide/K$_2$O Supported Catalyst of the Present Invention

Transition alumina in the form of spheres (~1.8 diameter) procured from Sasol with surface area of 207 m$^2$/g was used for catalyst preparation. The alumina support (about 100 g) was heat treated in an oven at 120° C. for 16 hours in the presence of air. The dried alumina support, after cooling to room temperature, was used for catalyst preparation by incipient wetness impregnation method. The catalyst was prepared by incipient wetness impregnation of the support with an aqueous solution of vanadyl oxalate. The required quantity of vanadyl oxalate (7.56 g) and the required quantity of potassium nitrate (0.39 g) was dissolved in water (22.3 mL) and used for incipient wetness impregnation. The impregnation was carried out by contacting the impregnation solution with alumina support (26.2 g) at room temperature. The impregnated alumina support was then kept at room temperature for 12 hours and then dried at 120° C. for 16 hours. The dried sample was then calcined at 750° C. for 4 hours in air (flow rate, 8 ml g$^{-1}$ min$^{-1}$). After calcination the catalyst was cooled in presence of air and the catalyst was stored in an air tight container. The calculated composition of the catalyst corresponds to vanadium oxide—12 wt. %, K$_2$O—0.6 wt. % with remaining part comprising transition alumina Example 5

Catalyst Characterization

The surface areas (BET) of the catalysts were determined using a Micromeritics Tristar Surface Area and Porosity Analyzer (Micromeritics Instrument Corp., USA). Prior to measurements, the sample (~200 mg) was evacuated for 2 hrs at 300° C. to remove physically adsorbed water and N$_2$ physisorption was carried out at −196° C. The surface area results are given in Table 1 (surface area for Comparative Example 1 and inventive Example 3) and in Table 2 (surface area for Comparative Example 2 and inventive Example 4). From the data, it was determined that catalysts prepared using vanadyl oxalate as the vanadium oxide precursor had a higher surface area as compared to catalysts prepared using ammonium metavanadate dissolved in oxalic acid as the vanadium oxide precursor.

TABLE 1

| Example | Formulation | Vanadium precursor | BET SA ($m^2/g$) |
|---|---|---|---|
| — | Transistion alumina | — | 137 |
| Comparative Example-1 | 6.3% Vanadium oxide-0.6%$K_2O$/transition alumina | AMV + OA | 122 |
| Example-3 | 6.3% Vanadium oxide - 0.6%$K_2O$/transition alumina | $VOC_2O_4 \cdot 2H_2O$ | 134 |

TABLE 2

| Example | Formulation | Vanadium precursor | BET SA ($m^2/g$) |
|---|---|---|---|
| — | Transition alumina | — | 207 |
| Comparative Example-2 | 12% Vanadium oxide - 0.6%$K_2O$/transition alumina | AMV + OA | 45 |
| Example-4 | 12% Vanadium oxide $_5$-0.6%$K_2O$/transition alumina | $VOC_2O_4 \cdot 2H_2O$ | 79 |

Example 6

Catalyst Testing

The dehydrogenation activities of the catalysts were measured in a tubular fixed-bed quartz reactor. The details of catalyst loading and reactor were as follows: catalyst weight=3.5 g, catalyst particle size=0.4-0.5 mm, reactor ID=16 mm, reactor OD=19 mm. Isobutane (99.9 vol. %) was used as the feed. Quartz chips with size of 1-1.4 mm were loaded above the catalyst bed. Nitrogen purge separated dehydrogenation and catalyst regeneration/oxidation and reduction with hydrogen. The total feed flow in the dehydrogenation step was GHSV=600 mLh$^{-1}$g$^{-1}$. The reactor outlet gases were analyzed by online gas chromatograph (Agilent 6890, Agilent Scientific Instruments, USA) equipped with a flame ionization detector for hydrocarbon analysis and thermal conductivity detector for hydrogen analysis. The reactant and products flow rates were measured using Ritter type wet gas flow meter. The reactor was operated at atmospheric pressure and in a cyclic mode with the following steps:
1. Oxidation in air at 650° C. for 30 min;
2. Purge with nitrogen at 650° C. for 5 min;
3. Reduction with $H_2$ at 650° C. for 6 min;
4. Cooling with nitrogen from 650° C. to 585° C. with 40 min. hold at 585° C.;
5. Dehydrogenation of isobutane at 585° C. for 21 min; and
6. GC analysis at 20$^{th}$ minute from the start of the isobutane feed.
7. Steps 1-6 were repeated for 30 cycles for before aging of the catalysts and 15 to 20 cycles after aging of the catalysts.

Figure 2A:
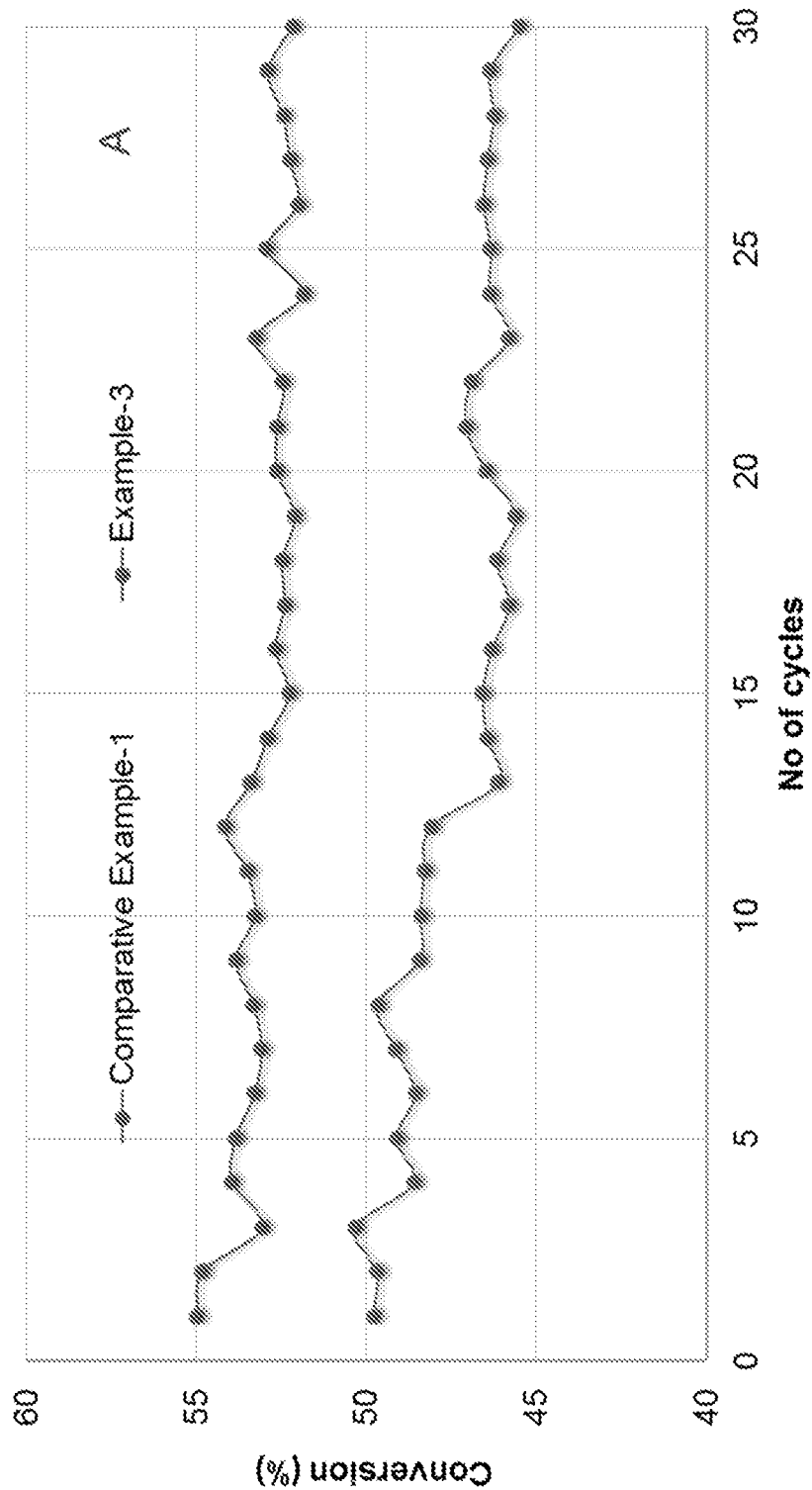
FIG. 2A shows isobutane conversion for a comparative catalyst and the catalyst of the present invention, both made from the same starting alumina.
Figure 2B:
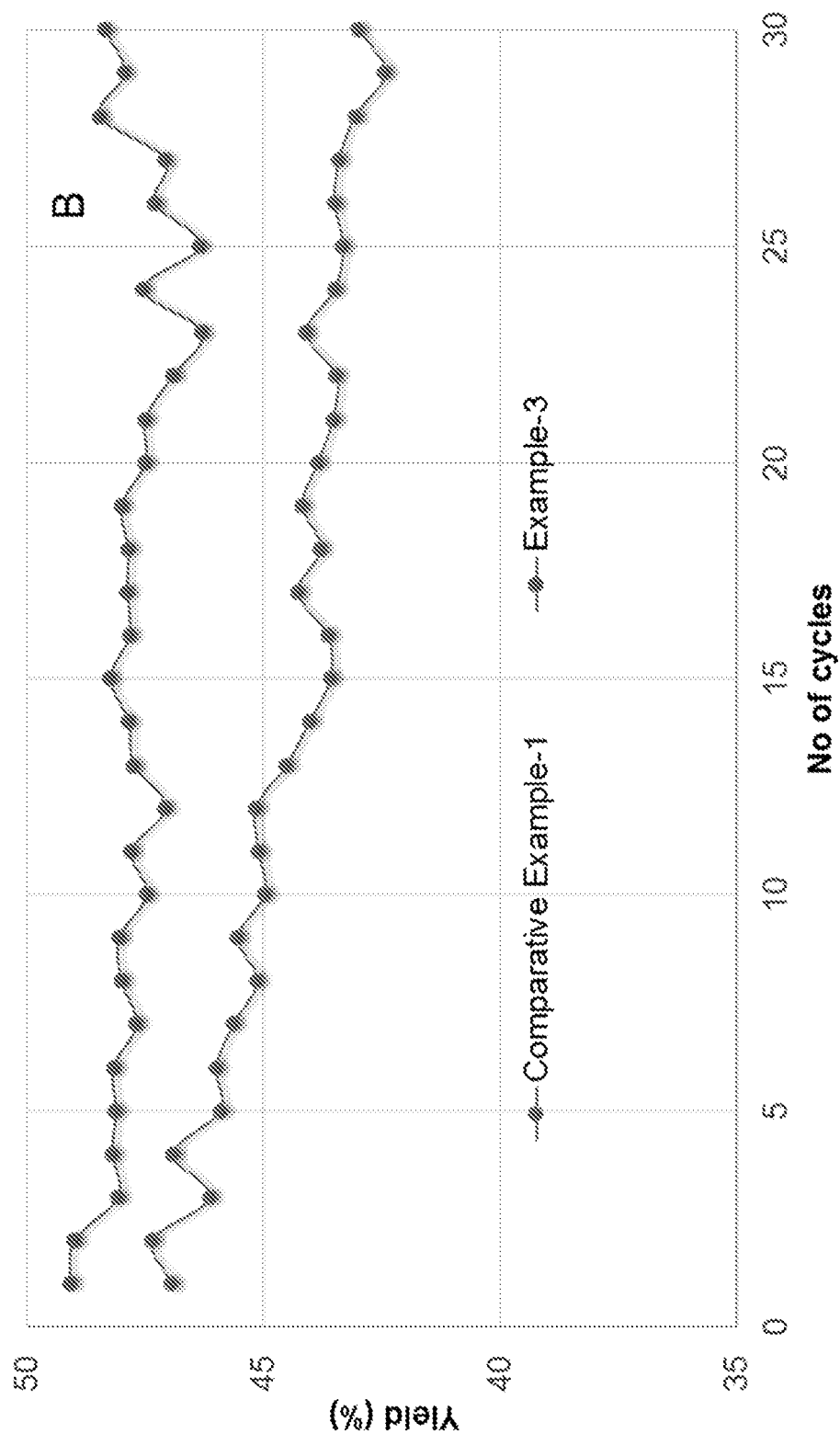
FIG. 2B shows isobutylene yield for a comparative catalyst and the catalyst of the present invention, both made from the same starting alumina.
Figure 3A:
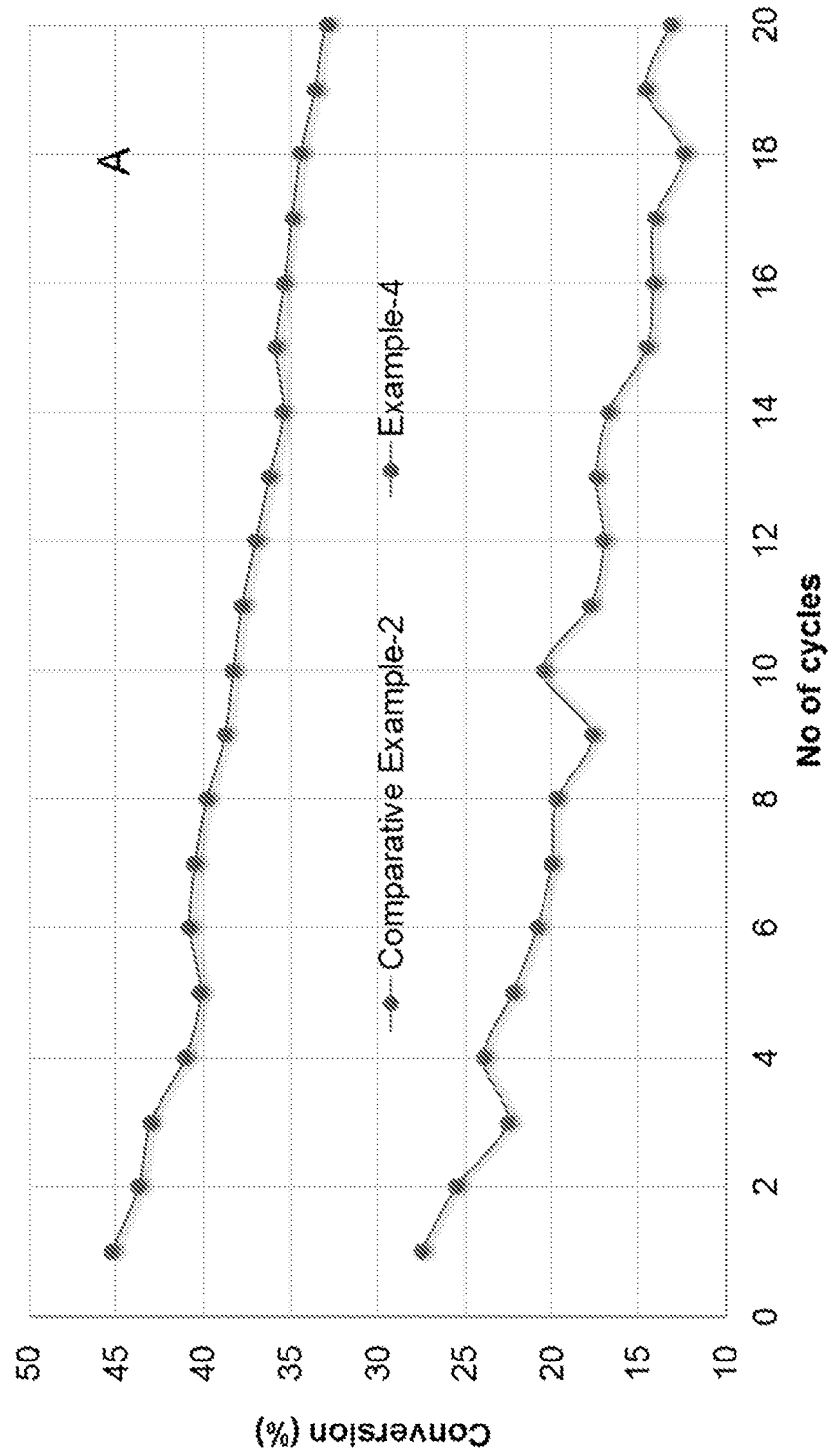
FIG. 3A shows isobutane conversion for a comparative catalyst (bottom line) and the catalyst of the present invention (top line), both made from the same starting alumina.
Figure 3B:
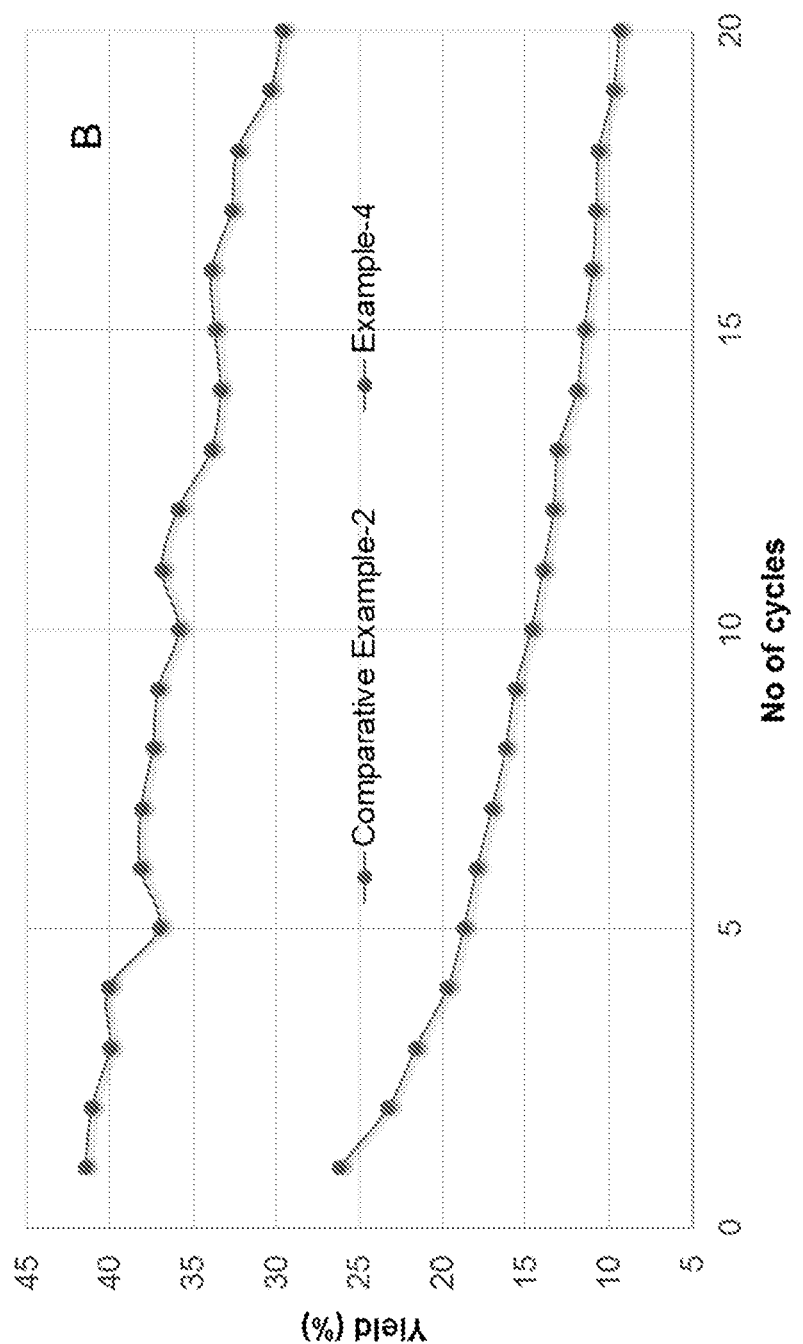
FIG. 3B shows isobutylene yield for a comparative catalyst (bottom line) and the catalyst of the present invention (top line), both made from the same starting alumina.

The isobutane dehydrogenation results are presented in FIGS. 2A and 2B (Examples 1 and 3) and FIGS. 3A and 3B (Examples 2 and 4). From the data, it was determined that catalysts prepared using vanadyl oxalate dissolved in water as the vanadium oxide precursor had higher isobutane conversion and isobutylene yield as compared to catalysts prepared using ammonium metavanadate dissolved in aqueous oxalic acid as the vanadium oxide precursor.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A method of preparing an alkane dehydrogenation catalyst, the method comprising:
   (a) contacting a transition alumina support with an aqueous solution comprising a vanadium carboxylate material and an alkali metal oxide precursor comprising an alkali metal solubilized therein;
   (b) heating the contacted alumina support to remove the water and produce a catalyst precursor material in solid form; and
   (c) heating the solid catalyst precursor material in the presence of an oxidizing source at a temperature of 500 to 800° C. to produce an alumina supported catalytic material comprising vanadium oxide;
   wherein the catalyst has a surface area of 60 to 160 $m^2/g$.

2. The method of claim 1, wherein the vanadium carboxylate material is vanadium monocarboxylate, vanadium dicarboxylate, vanadium tricarboxylate, or any combination thereof.

3. The method of claim 2, wherein the vanadium carboxylate is vanadium dicarboxylate.

4. The method of claim 1, wherein step (b) heating comprises a temperature of 70 to 90° C.

5. The method of claim 1, wherein the vanadium carboxylate is vanadyl oxalate.

6. The method of claim 1, wherein the catalytic material comprises 2 to 20 wt. % of vanadium oxide.

7. The method of claim 1, wherein the step (c) heating is sufficient to convert the alkali metal oxide precursor to an alkali metal oxide.

8. The method of claim 7, wherein the catalytic material consists of 2 to 13 wt. % of vanadium oxide and 0.1 to 1 wt. % $K_2O$ with balance being transition alumina.

9. The method of claim 1, wherein the catalytic material comprises 0.1 to 2 wt. % of the alkali metal oxide.

10. The method of claim 1, wherein the alkali metal is potassium.

11. The method of claim 1, further comprising the step of drying a moisture-containing transition alumina support to produce the transition alumina support.

12. A catalyst for non-oxidative dehydrogenation of alkanes, the catalyst comprising vanadium oxide derived from vanadyl oxalate and an alkali metal dopant, wherein the catalyst has a surface area of 60 to 160 $m^2/g$.

13. The catalyst of claim 12, wherein the dopant is potassium oxide.

14. The catalyst of claim 12, wherein the catalyst consists of vanadium oxide, potassium oxide, and transition alumina.

15. The catalyst of claim 14, wherein the catalyst consists of 2 to 20 wt. % vanadium oxide, 0.1 to 2 wt. % $K_2O$, and 78 to 97.9 wt. % transition alumina.

16. The catalyst of claim 12, wherein the catalyst further comprises a support.

17. A process for production of alkanes, the process comprising contacting the catalyst of claim 12 with a feed source comprising an alkane at a temperature of 400° C. to 800° C. to produce a product stream comprising an alkene, wherein the alkane is isobutane and the alkene is isobutene.

18. The process of claim 17, wherein the contacting is done in the absence of oxygen and/or halogenated alkanes.

19. The process of claim 17, further comprising:
  (i) heating the catalyst at 400 to 800° C. in the presence of an oxidizing source prior to contacting;
  (ii) removing the oxidizing source; and
  (iii) heating the catalyst at 400 to 800° C. in the presence of a reducing source.

* * * * *